(12) United States Patent
Pierson (10) Patent No.: US 8,052,421 B2
(45) Date of Patent: Nov. 8, 2011

(54) DISPENSING SYRINGE HAVING MULTIPLE BARRELS FOR DISCHARGING A DENTAL COMPOSITION

(75) Inventor: Paul R. Pierson, Camden, DE (US)

(73) Assignee: Dentsply International, Inc., York, PA (US)

( * ) Notice: Subject to any disclaimer, the term of this patent is extended or adjusted under 35 U.S.C. 154(b) by 0 days.

(21) Appl. No.: 12/587,417

(22) Filed: Oct. 7, 2009

(65) Prior Publication Data
US 2010/0028831 A1 Feb. 4, 2010

(51) Int. Cl.
*A61C 5/04* (2006.01)
(52) U.S. Cl. .......................................................... 433/90
(58) Field of Classification Search ............... 433/89, 433/90, 80, 88; 222/137, 309, 326, 327, 222/340, 341, 390, 145.6, 386; 604/118, 604/187, 208–211, 224, 82–84, 121, 125, 604/191, 141, 151, 154, 155
See application file for complete search history.

(56) References Cited

U.S. PATENT DOCUMENTS

| | | | |
|---|---|---|---|
| 3,002,517 A * | 10/1961 | Pitton ............................ 401/172 |
| 4,479,781 A * | 10/1984 | Herold et al. .................. 433/90 |
| 4,674,980 A | 6/1987 | Ibsen et al. |
| 4,920,082 A | 4/1990 | Danielson |
| 5,172,807 A * | 12/1992 | Dragan et al. ................ 206/219 |
| 5,304,586 A | 4/1994 | Hammesfahr et al. |
| RE34,937 E | 5/1995 | Ibsen et al. |
| 2004/0110112 A1* | 6/2004 | Xie et al. ......................... 433/89 |
| 2007/0072146 A1 | 3/2007 | Pierson |

FOREIGN PATENT DOCUMENTS

| | | |
|---|---|---|
| DE | 10128611 A1 | 6/2001 |
| DE | 20313778 U1 | 8/2003 |
| EP | 1426017 A2 | 6/2004 |
| WO | 2007041266 A1 | 4/2007 |

* cited by examiner

*Primary Examiner* — Sunil K Singh
(74) *Attorney, Agent, or Firm* — Douglas J. Hura; Leana Levin; David A. Zdurne

(57) ABSTRACT

A dispensing syringe for dispensing a multi-component dental composition, preferably a two component composition, is provided. The syringe includes a syringe body with multiple elongated barrels for storing the components of the composition; a threaded plunger rod assembly; and a rotatable, threaded connector knob. Preferably, the syringe body has a double-barrel structure and the plunger rod assembly includes two plunger rods that slide within the barrels. The threaded knob has a through-bore with a continuous internal thread for engaging the outer threads of the first and second plunger rods. A dental practitioner manually rotates the knob to displace the first and second plunger rods and discharge the components. The dispensing syringe may further include a dispensing tip containing a static mixing element for mixing the components and dispensing the mixed composition.

21 Claims, 10 Drawing Sheets

DISPENSING SYRINGE HAVING MULTIPLE BARRELS FOR DISCHARGING A DENTAL COMPOSITION

BACKGROUND OF THE INVENTION

1. Field of the Invention

The present invention relates generally to a dispensing device for dispensing a multi-component composition such as, for example, epoxy cements, adhesives, medicaments, and dental materials. More particularly, the invention relates to a dispensing syringe having a syringe body with at least two elongated barrels. Each barrel is used to store and dispense a component of the composition. The dispensing syringe may include a dispensing tip containing a static mixing element for mixing the components and then dispensing the mixed composition. Preferably, the syringe is used to mix and dispense a dental composition such as, for example, a dental cement or adhesive.

2. Brief Description of the Related Art

Dental professionals use dispensing syringes for storing, mixing, and dispensing a wide variety of dental compositions. For instance, a dentist may use a dispensing syringe in preparing and dispensing dental impression materials, temporary restorative materials, cements and adhesives. Such dental compositions can be self-curable, light-curable, or dual-curable. The dental compositions are cured and hardened by different chemical mechanisms to form a strong and durable material. In one example, a dentist uses a self-curing dental cement, which is prepared from two paste components, for bonding crowns, bridges, veneers, and other restoratives to the tooth. Generally, about 0.25 to about 0.5 mL of dental cement is used in such applications. One component used to make the dental cement is a base paste and the other component is a catalyst paste. The base paste typically contains polymerizable monomers such as methacrylate or acrylate monomers; a free-radical polymerization accelerator such as a tertiary amine; and fillers such as silica, glasses, or alumina. Meanwhile, the catalyst paste typically includes a polymerizable monomer, a free-radical polymerization initiator such as a peroxide, and fillers.

The base and catalyst pastes can be measured and mixed together by hand or an auto-mix syringe system can be used. Dentists often prefer working with auto-mix systems, because the base and catalyst pastes are stored in commercially-available cartridges and can be dispensed from the cartridges in a pre-determined volume ratio to form an optimally mixed composition. The dentist can save time using such auto-mix systems and avoid mixing ratio errors. A "double barrel" dispensing syringe is often used in auto-mix systems. In general, the double barrel syringe includes two separate, elongated barrels or chambers that are arranged in a side-by-side configuration. The barrels are sealed, and the base paste is stored in one barrel, while the catalyst paste is stored in the other barrel. The barrels are connected to a dispensing tip. In practice, the dentist pushes on the plunger of the syringe to force the base and catalyst pastes from their respective barrels and into the dispensing tip. The dispensing tip typically contains a static mixer. As the base and catalyst pastes are extruded through the static mixer, they are combined and mixed together to form the final, mixed dental cement. Then, the dentist can dispense the cement onto the desired target, for example, a temporary crown, and mount the crown over a "crown-prepped" tooth in the mouth of the patient.

In another example, the double barrel syringe is used to dispense a dental composition used to make the temporary crown. Generally, about 1 to about 2 mL of material is used to make the temporary crown. Normally, the dentist places a temporary crown on the tooth to cover and protect the tooth, until a dental laboratory makes the permanent crown. The temporary crown is made from a polymeric material such as an acrylic. More particularly, a polymerizable material, which is prepared from base and catalyst pastes, can be used to form the temporary crown. In a manner similar to the above-described method used to make dental cements, the base and catalyst pastes are stored in the barrels of the syringe until it is time to prepare the crown. Then, the base and catalyst pastes are forced from their respective barrels and into the dispensing tip containing the static mixing element. The pastes are mixed in the dispensing tip and the resulting composition is dispensed onto an alginate impression, plastic matrix, or other material to make the temporary crown.

One example of a double barrel syringe is illustrated in Drake, U.S. Pat. No. 4,538,920. This patent discloses a dispensing device having a having a pair of chambers for storing dental resins separately and a pair of plungers that are forced into the chambers to discharge the resins. The device further includes a static-mixing element housed with an exit conduit and a discharge nozzle. The static-mixing element is held in a fixed position in order to maintain a predetermined alignment of a first blade in the static-mixing element relative to the two streams of resinous material. The patent suggests that this is necessary to achieve maximum mixing of the two streams of resinous materials in the discharge nozzle.

Spehar et al., U.S. Pat. No. 4,753,536 describes a double barrel syringe with two compartments for storing two separate dental polymeric materials, a discharge assembly, and a nozzle assembly for dispensing the material. The nozzle assembly comprises a common nozzle, a static-mixing element with an arm extending from one end. The static mixer is arbitrarily inserted into the bore of the nozzle. The discharge of the polymeric material from the compartments causes the static mixer to turn until the arm engages an end stop. The end stop prevents further rotation of the arm as material is fed into the nozzle, thereby allowing the mixer to intermix the two materials from the storage compartments.

Sawhney et al., U.S. Pat. No. 6,394,314 discloses a double-barreled syringe for storing two viscous dental substances. The syringe includes a double-plunger assembly with juxtaposed first and second plungers and a mixing tip. The plungers are attached at their distal end to a disc-shaped thumb-rest so that when the thumb-rest is depressed the plungers move forward in tandem and discharge the substances into the mixing tip. The mixing tip is detachable after the tip is locked to the syringe body, so a person can replace the tip with a locking cap.

Bills, U.S. Pat. No. 6,732,887 discloses a double barrel syringe having detachably connecting barrels, detachably connecting plungers, and an applicator tip. The barrels can be manufactured at different times and out of different materials so that they have different colors, insulating properties, and opaque or translucent properties. The plunger assembly includes a first plunger, which is pressed to force out the first component from the first barrel and a second plunger, which is pressed to force out the second components from the second barrel.

Xie et al., U.S. Pat. No. 6,843,652 describes the device as being particularly suitable for delivering a single dose quantity of a two-component dental impression material. The double barrel syringe includes a dispenser body having a first and second cylindrically shaped chamber, an actuator, a closure, and a dispenser tip. The first and second components of the material are stored in their respective chambers. The actuator includes first and second plungers, which are adapted to slide within the first and second chambers and dispense the respective components. The plungers are connected at their distal end by a thumb pad. A dental professional depresses the thumb pad when he or she is ready to dispense the material. This causes the plunger rods to move in unison and dispense the first and second components simultaneously.

In the double-barrel syringes described in the above-mentioned patents, a person must depress the syringe plunger to force the resin components from the barrels and into a mixing/dispenser tip. These double-barrel syringes are generally effective. One drawback, however, is that it can be difficult to dispense resins having a thick consistency using such conventional double-barrel syringes. A sufficient amount of pressure must be exerted on the thumb pad or other actuator handle, and it can be difficult to apply this force while handling the syringe at the same time.

Other dual chamber systems for dispensing dental material are known including hand-held ejector-type guns as described in Wilcox et al., U.S. Pat. Nos. 5,624,260 and 5,722,829. These gun-like applicators include a cartridge having a first chamber and a second chamber for storing dental materials and a pair of plungers for dispensing the materials through a discharge tip. The applicator further includes a handle extending from a body portion and an arm located next to the handle and movable relative to the body. To advance the plungers, the arm is swung about the pivot point. As the arm moves toward the handle, the lower front edge of a pawl engages the ratchet teeth on the plungers, there causing the plungers to simultaneously advance. These applicator guns can provide an effective system for dispensing highly viscous resin materials. The applicator guns increase the mechanical advantage of the operator. This allows the operator to hold the gun in various orientations and dispense the material in difficult to reach areas of a patient's oral cavity. However, such applicator guns have several disadvantages including their added bulk, complexity of operation, and relatively high cost to manufacture.

In view of the drawbacks with some conventional dispensing devices for dental materials, there is a need in the industry for an improved dispensing device. Particularly, the syringe device should be capable of dispensing two components of a dental composition simultaneously and in precisely metered quantities. In addition, a dental professional should be able to handle and use the syringe easily. A user should not be required to spend a large block of time loading the components into the barrels, mixing, and dispensing them accordingly. The dispensing mechanism should be relatively simple and not require the interaction of many small parts. The syringe should be economically feasible to manufacture. Moreover, the syringe should have a dispensing mechanism, which provide a mechanical advantage to the user. Such a syringe would be particularly valuable to users who need ergonomic assistance in dispensing the material from the syringe. The present invention provides a dispensing syringe having the foregoing features and characteristics. These and other objects, benefits, and advantages of this invention are evident from the following description and illustrated embodiments.

SUMMARY OF THE INVENTION

The present invention relates to a dispensing syringe for dispensing a multi-component dental composition, preferably a two component composition. In one embodiment, the syringe includes a syringe body having a double barrel structure. The first elongated barrel is used for storing and discharging a first component of the composition. The first barrel has an opening for receiving a first plunger rod and an exit port for discharging the first component. The second elongated barrel is used for storing and discharging a second component of the composition. The second barrel has an opening for receiving a second plunger rod and an exit port for discharging the second component.

The syringe further includes a plunger rod assembly comprising a rearward stop plate attached to a first threaded plunger rod and a second threaded plunger rod. The first and second plunger rods are arranged in parallel and move jointly within the first and second barrels, respectively. The plunger rods may be outfitted with elastomeric pistons at their forward-facing end portions for forcing the components through the exit ports. The syringe also includes a rotatable knob for connecting the threaded plunger rod assembly to the syringe body. The threaded knob has a through-bore with a continuous internal thread for engaging the outer threads of the first and second plunger rods. As the knob is rotated, the first and second plunger rods move together within their respective barrels to discharge the components of the composition.

The syringe body may include a dispensing tip for receiving the first and second components of the composition. The dispensing tip then delivers the composition to a desired target area. The dispensing tip may further be outfitted with a static mixing element, which combines and mixes the components of the composition. The mixed composition is then dispensed through the nozzle of the dispensing tip.

In other embodiments of the syringe of this invention, a syringe having more than two barrels can be used to dispense a multi-component composition. For example, the syringe may have three (3) or four (4) barrels for dispensing a three or four component dental composition.

BRIEF DESCRIPTION OF THE DRAWINGS

The novel features that are characteristic of the present invention are set forth in the appended claims. However, the preferred embodiments of the invention, together with further objects and attendant advantages, are best understood by reference to the following detailed description in connection with the accompanying drawings in which:

DETAILED DESCRIPTION OF THE PREFERRED EMBODIMENTS

Figure 1:
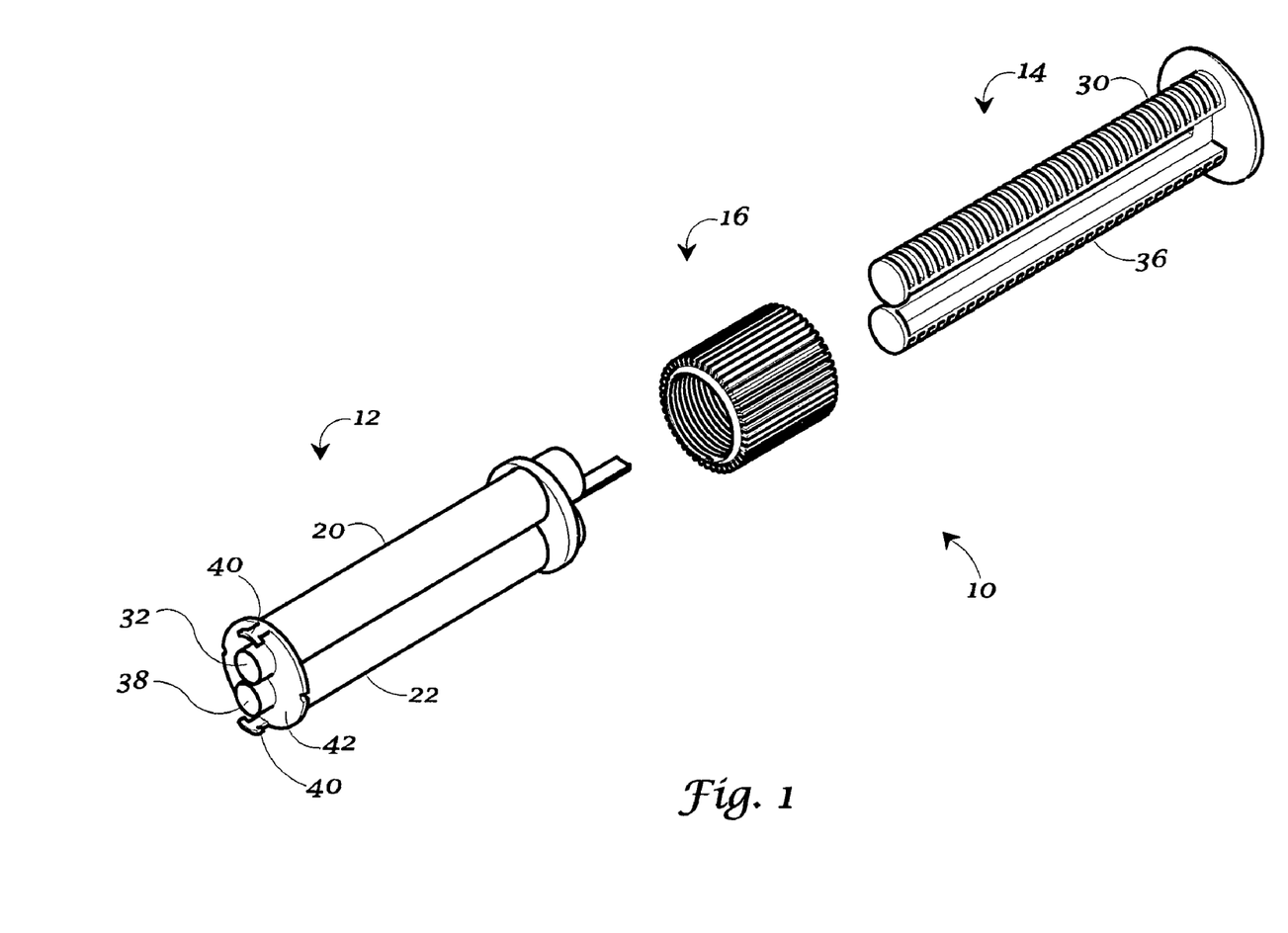
FIG. 1 is an exploded, perspective view of one embodiment of the dispensing syringe of this invention.
Figure 2:
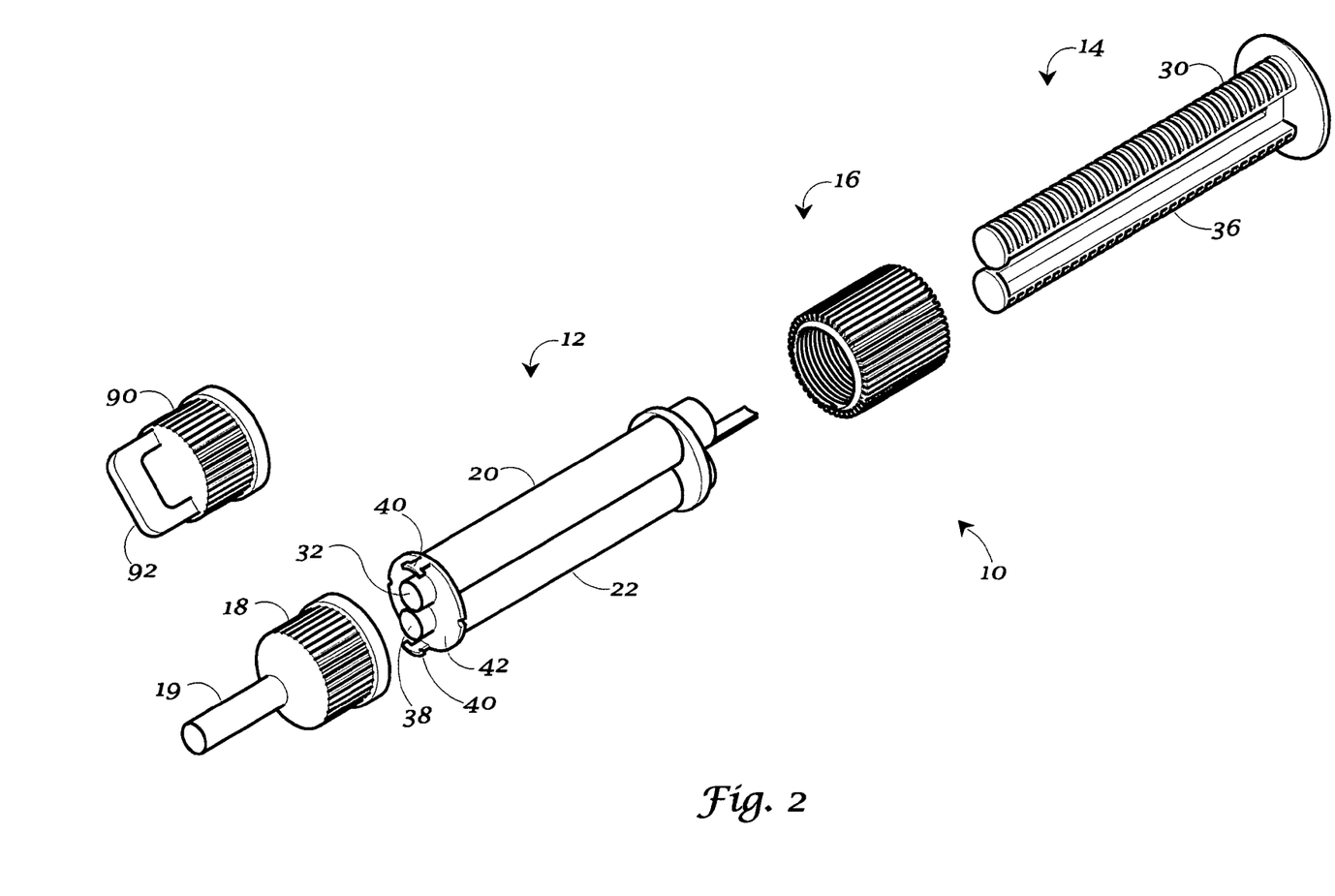
FIG. 2 is an exploded, perspective view of one embodiment of the dispensing syringe of this invention showing the syringe with a dispensing tip and twist cap.

Referring to FIG. 1, one embodiment of the dispensing syringe device (10) of the present invention is generally shown. The dispensing syringe (10) includes a double-barreled syringe body (12); a split-threaded plunger rod assembly (14); and a rotatable, threaded, connector knob (16). A dispensing tip (18) is preferably installed at the distal end of the syringe body (12) as shown in FIG. 2. The dispensing tip (18) is used for mixing first and second components of a dental composition and then dispensing the mixed composition onto a selected target such as, for example, a plastic matrix for making a temporary crown or bridge. In the following detailed description, we will primarily refer to the syringe device (10) containing the dispensing tip (18) as illustrated in FIG. 2. It should be understood, however, that the dispensing tip (18) is an optional feature of the syringe (10), and it may be desirable to use the syringe (10) without the dispensing tip (18) in some dental procedures.

Figure 3:
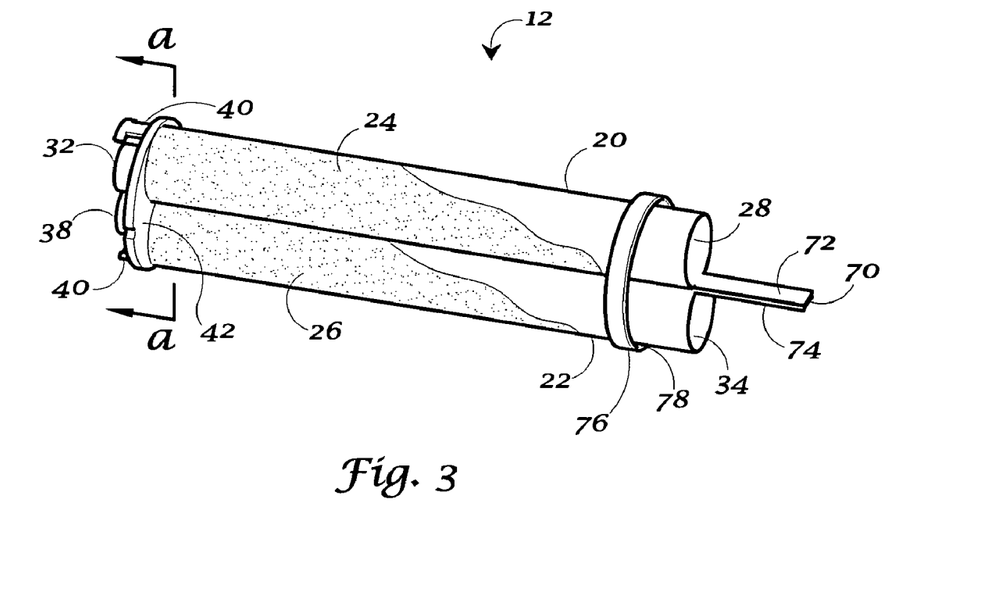
FIG. 3 is a perspective view of one embodiment of the syringe body, which is a component of the dispensing syringe of this invention.
Figure 3A:
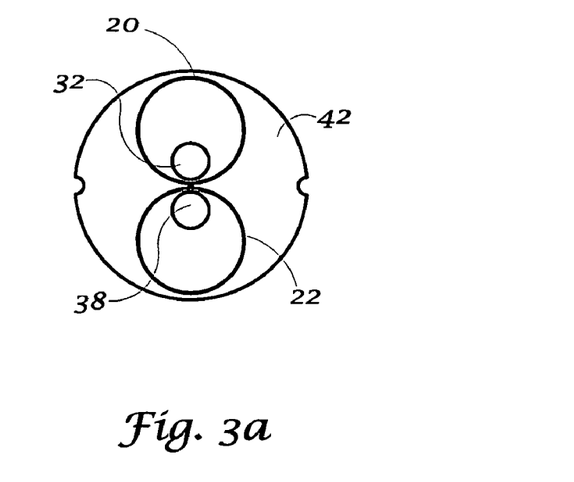
FIG. 3A is a cross-sectional view of the syringe body shown in FIG. 3 taken along lines A-A.

FIG. 3 shows a close-up, perspective of the syringe body (12) including first and second cylindrically-shaped barrels or chambers (20, 22), which are used for holding first and second components (24, 26) of a dental composition. The first and second barrels (20, 22) extend along the length of the syringe body (12) in parallel and are integrally connected to each other. The first barrel (20) includes a proximate opening (28) adapted for receiving a first plunger rod (30). A projecting exit port (32) adapted for discharging the first component (24) into the dispensing tip (18) is located at the distal end of the barrel (20). Likewise, the second barrel (22) includes a proximate opening (34) for receiving a second plunger rod (36) and a projecting exit port (38) for discharging the second component (26) into the dispensing tip (18). As shown in FIG. 3, the distal end of the syringe body (12) can include side flanges (40) for connecting the dispensing tip (18) thereto. A circular retainer plate (42) is integrally connected to the distal end of the syringe body (12) and is adapted for receiving the dispensing tip (18) as the tip is fastened to the syringe body. The exit ports (32, 38) extend through the plate (42). The dispensing tip (18) is secured over the exit ports (32, 38) and to the retainer plate (42). Thus, the first and second components (24, 26) can be discharged from the first and second barrels (20, 22) and through the exit ports (32, 38) to the dispensing tip (18).

The syringe body (12) and other pieces of the syringe device (10) can be constructed from any suitable material and are preferably made from a moldable plastic composition. Injection-molding and other manufacturing processes can be used to fabricate the syringe parts. The resulting plastic syringe (10) should be lightweight and durable. The syringe (10) can be constructed to a suitable size for storing and dispensing the dental composition. Double barrel syringes for dental compositions have been made historically in such sizes as to hold 2.5 mL to 10 mL of product. Further, it should be understood that the double-barrel syringe (10) with cylindrically shaped first and second barrels (20, 22) represents only one embodiment of the syringe device of this invention. The first and second barrels (20, 22) can have any suitable cross-sectional shape for holding and dispensing the dental composition. For example, in other embodiments, the first and second barrels (20, 22) can have a "D-shaped" or "wedge-shaped" cross-sectional structure.

Figure 4:
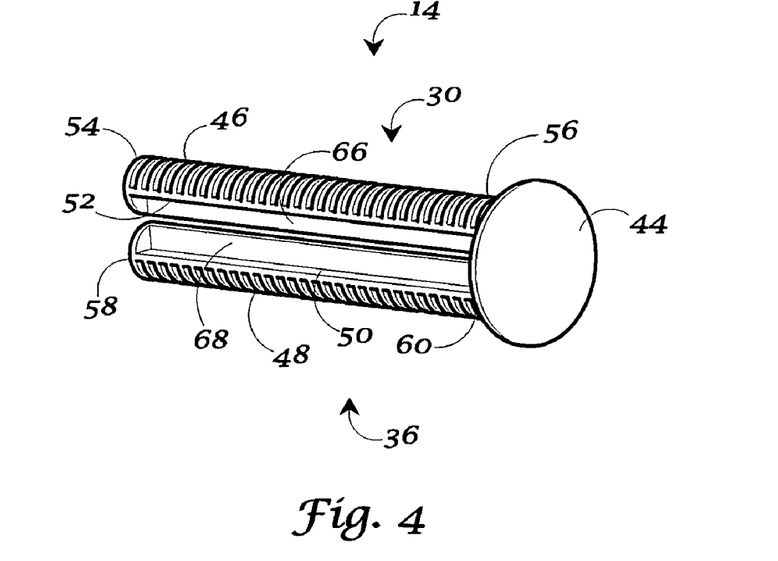
FIG. 4 is a perspective view of one embodiment of the plunger rod assembly, which is a component of the dispensing syringe of this invention.
Figure 4A:
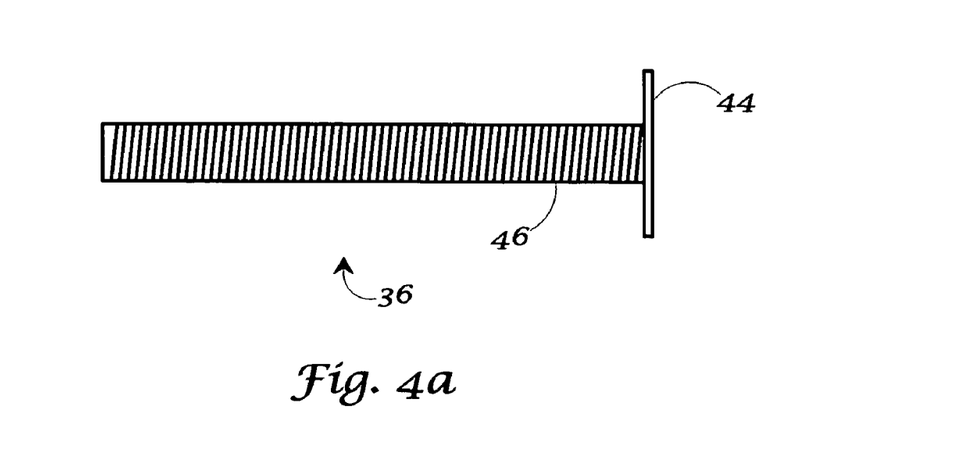
FIG. 4A is a side perspective view of the plunger rod assembly shown in FIG. 4.
Figure 4B:
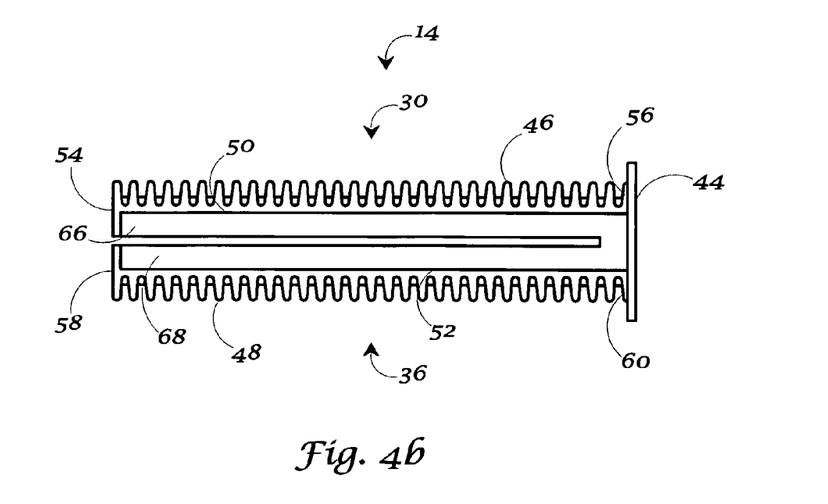
FIG. 4B is an overhead perspective view of the plunger rod assembly shown in FIG. 4.

Referring to FIGS. 4, 4A, and 4B, the plunger rod assembly (14) is shown including a rigid rearward stop plate (44) and first and second, threaded plunger rods (30, 36), which are attached thereto. The plunger rods (30, 36) are arranged in parallel and separated by a slight gap therebetween. Each plunger rod (30, 36) includes an outer threaded edge (46, 48) and an inner non-threaded edge (50, 52), respectively. The second thread (48) located on the outer edge of the second plunger rod (36) is a continuation of the oppositely positioned first thread (46) located on the outer edge of the first plunger rod (30) as shown in FIG. 4B. In other words, the outer thread of the plunger rod assembly (14) can be considered a split-thread comprising first and second outer threaded portions (46, 48). The first plunger rod (30) further includes a forward-facing end portion (54) for forcing the first component (24) into the dispensing tip (18), and an opposing rear-facing end portion (56) attached to the stop plate (44). The second plunger rod (36) also includes a forward-facing end portion (58) for forcing the second component (26) into the dispensing tip (18) and an opposing rear-facing end portion (60) attached to the stop plate (44).

Figure 5:
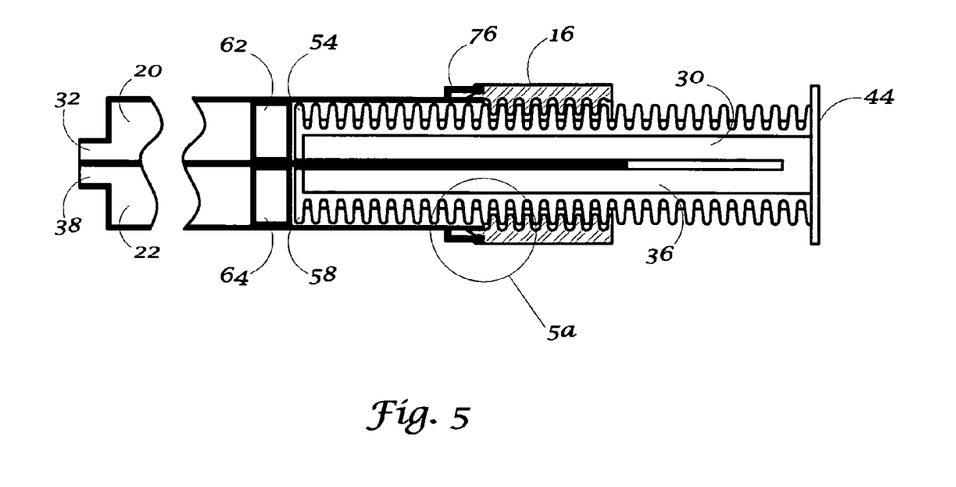
FIG. 5 is a cross-sectional view of one embodiment of the dispensing syringe of this invention.

Turning to FIG. 5, each plunger rod (30, 36) may be outfitted with a piston (62, 64) at its respective forward-facing portions (54, 58). The first and second pistons (62, 64) typically are made of an elastomeric material that effectively seals the respective plunger rods (30, 36) from the composition that is being dispensed through the barrels (20, 22). However, it is recognized that other sealing components such as, for example, flanges or O-rings, which provide a seal and wipe the side-walls of the barrels (20, 22) as the plunger rods (30, 36) are being actuated, may be installed in accordance with this invention. The elastomeric pistons (62, 64) may be separately manufactured components that are snap-fitted or otherwise connected to the forward-facing portions (54, 58) of the plunger rods (30, 36). Alternatively, the pistons (62, 64) may be molded to the ends (54, 58) of the plunger rods (30, 36).

The pistons (62, 64) slide along the inner sidewalls of the barrels (20, 22) as the plunger rods (30, 36) are driven into the barrels (20, 22) by manually turning the threaded, connector knob (16). The pistons (62, 64) force the first and second components (24, 26) into the dispensing tip (18) by this sliding/sealing mechanism. As discussed above, the first and second plunger rods (30, 36) are arranged in parallel and preferably connected at their respective rear-facing end portions (54, 58) by the rigid stop plate (44). This structure allows for unison displacement of the plunger rods (30, 36). The plunger rods (30, 36) move jointly within the barrels (20, 22) so that the first and second components (24, 26) are delivered simultaneously into the dispensing tip (18). The turning of the threaded, connector knob (16) and displacement of the plunger rods (30, 36) within the barrels (20, 22) are described in further detail below.

The rotatable, threaded, connector knob (16) (FIGS. 1 and 2) of the dispensing syringe (10) serves various functions. The knob (16) first provides a means for coupling the plunger rod assembly (14) to the syringe body (12). As shown in FIG.

Figure 6:
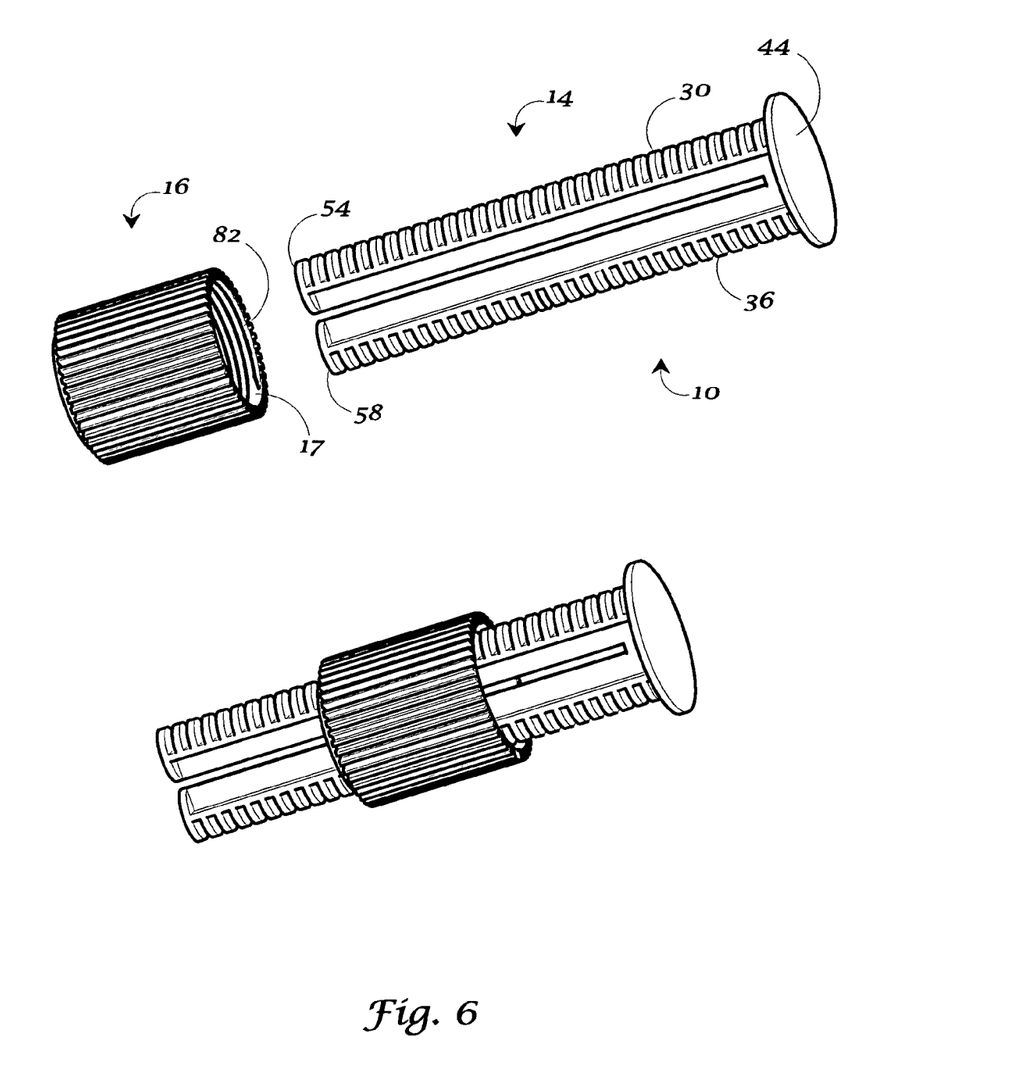
FIG. 6 is a perspective view of the plunger rod assembly and connector knob showing the plunger rods being inserted through the connector knob during the assembly of the dispensing syringe.

6, in assembling the syringe device (10), the plunger rods (30, 36) are inserted first through the through-bore (17) of the connector knob (16) so that their forward-facing end portions (54, 58) extend about one-quarter (¼) inches from the knob. The plunger rods (30, 36) can be more easily inserted through the connector knob (16) by flexing the plunger rods (30,36) slightly inwards. After being inserted through the bore of the knob (16), the threaded plunger rods (30, 36) will resume their natural shape and flex outwardly so as to engage the internal threads (82) of the connector knob (16). The intermating of the threaded plunger rods (30, 36) with the internal threads (82) of the connector knob (16) is described in further detail below.

Next, the forward-facing end portions (54, 58) of the plunger rods (30, 36) are inserted into the first and second barrels (20, 22) of the syringe body (12), respectively. As shown in FIGS. 4-4B, the first and second inner, non-threaded edges (50, 52) of the plunger rods (30, 36) can each include a projecting radial fin (66, 68). The radial fins (66, 68) extend along the lengths of the inner, non-threaded edges (50, 52), respectively and radiate at an angle of about ninety degrees to the edges.

Referring back to FIG. 3, the syringe body (12) further includes a central supporting member (70) that extends from the proximate end of the syringe body (12). The supporting member (70) is positioned between the first and second proximate openings (28, 34). The supporting member (70) includes a first inner grooved segment (72), which is adapted for receiving the radial fin (66) of the first plunger rod (30), and a second inner grooved segment (74), which is adapted for receiving the radial fin (68) of the second plunger rod (36). The grooved segments (72, 74) thus can be used to help align and guide the plunger rods (30, 36) into the barrels (20, 22) when assembling and using the syringe (10). During assembly of the syringe (10), the radial fins (66, 68) engage and slide along the respective inner grooved segments (72, 74) as the plunger rods (30, 36) are inserted into the barrels (20, 22). The grooved segments (72, 74) of the supporting member (70) thus brace the plunger rods (30, 36). Furthermore, this supporting mechanism keeps the outer threads (46, 48) engaged with the internal threads (82) of the connector knob (16). Thus, the plunger rods (30, 36) are prevented from flexing inwardly under the incline pressure caused by the engaged threads during rotation of the connector knob (16).

The next step in the assembling of the syringe (10) involves snap-fitting or otherwise connecting the connector knob (16), with the plunger rod assembly (14) projecting therethrough, to the syringe body (12). This step can be performed in the following manner. First, as shown in FIG. 3, the syringe body (12) includes an outwardly extending circular ledge (76). The ledge (76) includes a recessed surface portion (78) adapted for receiving the connector knob (16). The ledge (76) is integrally connected to the syringe body (12) so that it surrounds the first and second barrels (20, 22).

Figure 7:
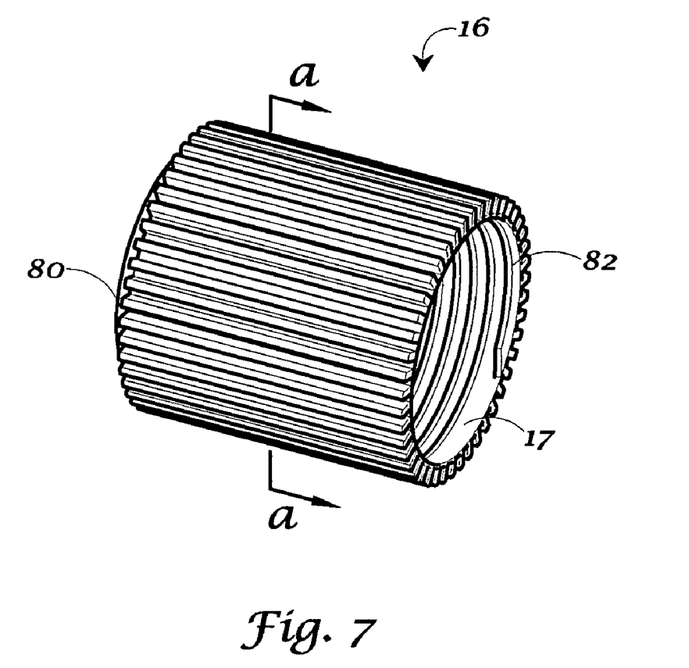
FIG. 7 is a perspective view of one embodiment of the connector knob, which is a component of the dispensing syringe of this invention.

Turning to FIG. 7, the knob (16) includes a circular locking flange or bead (80) projecting from its lower end portion. The knob (16) can be snap-fitted onto the ledge (76) of the syringe body (12) by pressing the circular locking flange (80) into the circular recessed surface portion (78) of the ledge. When the locking flange (80) and recessed ledge (76) are pressed together, they interlock to capture the connector knob (16). In this manner, the knob (16) securely connects the plunger rod assembly (14) to the syringe body (12). At the same time, the threaded, connector knob (16) is free to rotate about the longitudinal axis of the syringe body (12). Turning the securely fastened connector knob (16) causes the threaded plunger rods (30, 36) to translate forward and deliver the first and second components (24, 26) to the dispensing tip (18) as described in further detail below. The foregoing is an exemplary embodiment for fastening the connector knob (16) to the syringe body (12). It is recognized that other suitable fastening means can be used if desired.

Figure 5A:
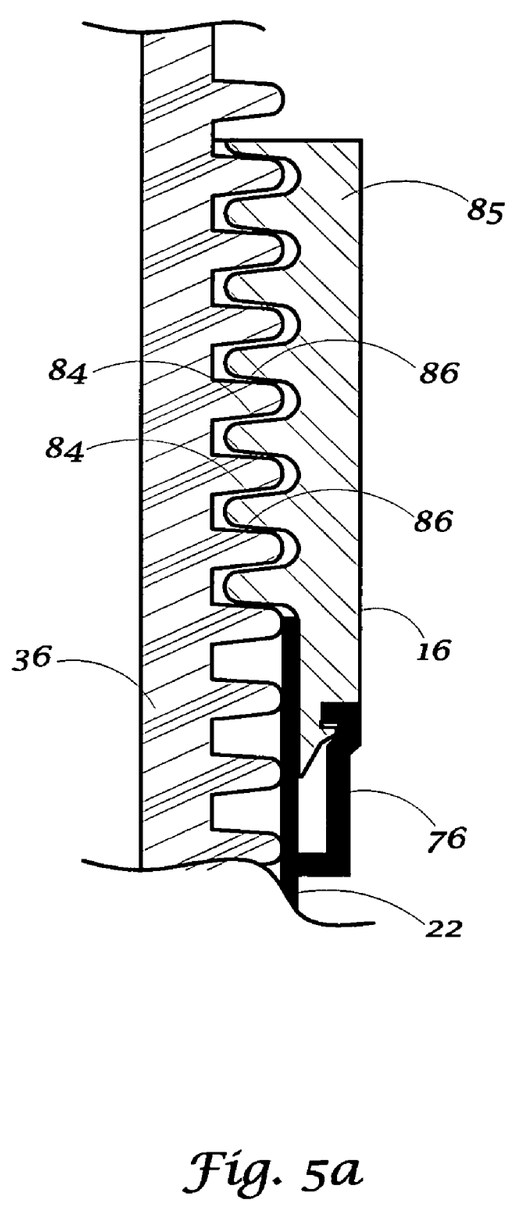
FIG. 5A is a close-up view of the area identified as "5a" in FIG. 5.
Figure 7A:
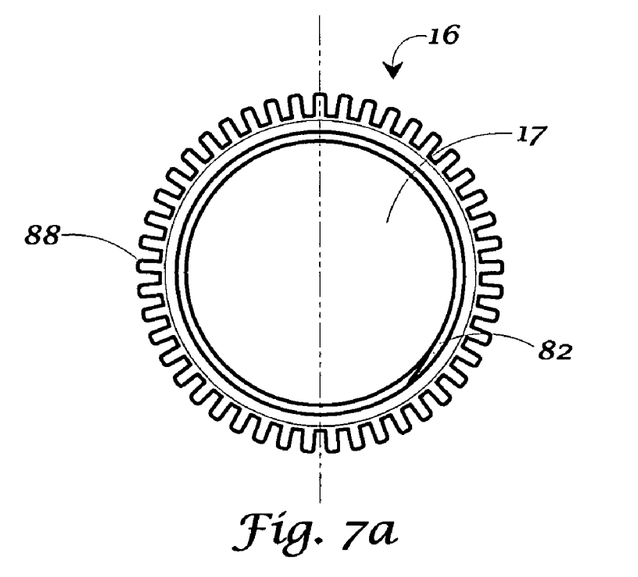
FIG. 7A is a cross-sectional view of the connector knob shown in FIG. 7 taken along lines A-A.

The connector knob (16) also provides a means for displacing the plunger rod assembly (14) and discharging the first and second components (24, 26) into the dispensing tip (18). Particularly, referring to FIGS. 7 and 7A, the threaded knob (16) has a through-bore (17) with a continuous internal thread (82) for engaging the outer threaded edges (46, 48) of the plunger rods (30, 36). The concentric internal thread (82) engages the complementary outer threads (46, 48) so that the threaded knob (62) is free to rotate. More particularly, the threaded knob (16) and each of the plunger rods (30, 36) can be considered to have a series of engaging teeth. This system of gear teeth, which includes the threaded connector knob (16) and threaded plunger rods (30, 36), functions in a manner similar to a planetary gear system, where the threaded knob (16) rotates about an axis and imparts axial motion to the threaded rods (30, 36). FIG. 5A shows a close-up view of the plunger rod (36) containing multiple teeth (84) and the threaded sleeve (85) of the knob (16) containing multiple teeth (86). The teeth (84, 86) are staggered in relation to each other so that the teeth (86) along the threaded sleeve (85) will conform to the recesses located between the teeth (84) of the plunger rod (36). As the threaded connector knob (16) is turned, the threaded plunger rods (30, 36) and threaded connector knob (16) interact with each other. The internal threads (82) of the connector knob (16) transfer axial motion to the plunger rods (30, 36). This causes the plunger rods (30, 36) to move together in a forward or rearward direction depending upon which direction the connector knob (16) is turned.

Figure 8:
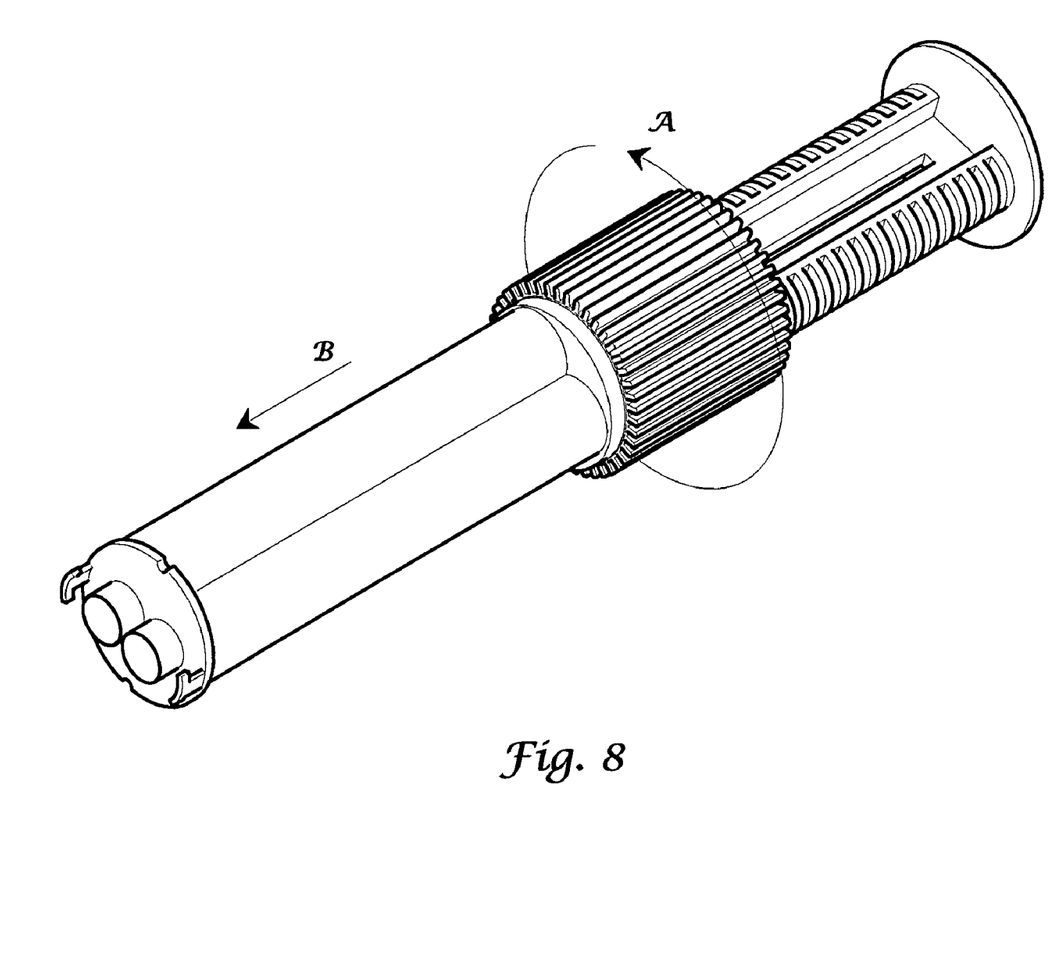
FIG. 8 is a perspective view of one embodiment of the dispensing syringe of this invention showing a composition being dispensed from the syringe as the connector knob is rotated in one direction.
Figure 9:
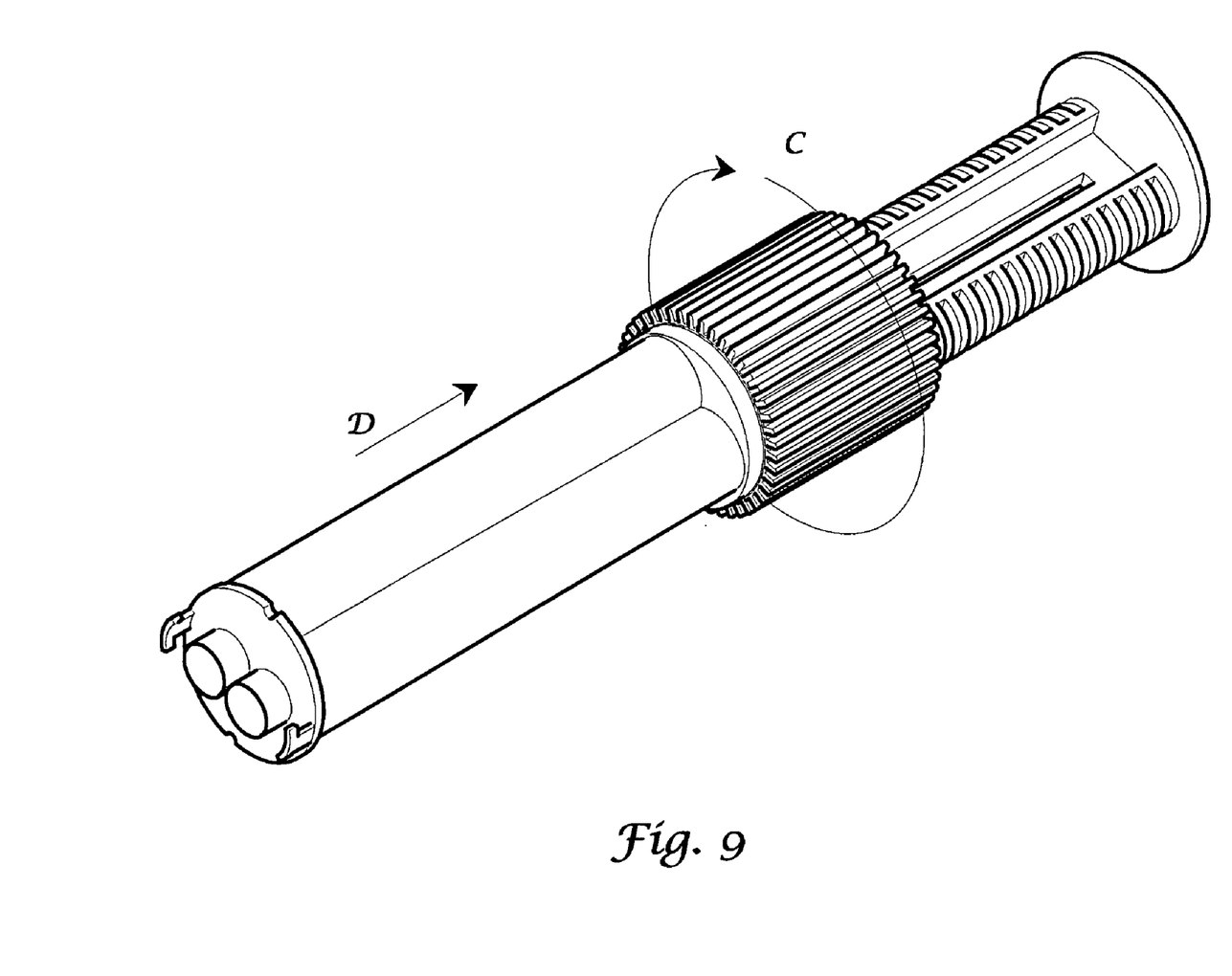
FIG. 9 is a perspective view of the dispensing syringe shown in FIG. 8 showing the connector knob being rotated in a direction opposite to the rotational direction shown in FIG. 8.

The rotational direction of the threaded plungers (30, 36) and connector knob (16) can be either right-handed or left-handed. For example, in one embodiment as illustrated in FIG. 8, a dental professional can grip the syringe body (12) with his or her right hand. The user can then grasp the rotatable knob between the thumb and finger of his or her left hand. The rotatable knob (16) can include ribs (88) on its outer surface for gripping ease. Then, the user rotates the knob (16) in a clockwise direction (when viewed from the rearward stop plate (44) connected to the plunger rods (30, 36)) to advance the rods forward and dispense the dental composition accordingly. Particularly, the connector knob (16) is rotated in the direction of the arrow A, and the plunger rods (30, 36) move together in the direction of Arrow B. Conversely, if a person rotates the connector knob (16) in the direction of the arrow C, the plunger rods will move together in the direction of Arrow D as shown in FIG. 9.

The optional dispensing tip (18) is attached to the distal end of the syringe body (12) so that it may receive the first and second components (24, 26), which are discharged from the first and second barrels (20, 22), respectively. Then, the components (24, 26) can be dispensed through the nozzle (19) of the dispensing tip (18) to the desired target. In practice, the first and second barrels (20, 22) of the syringe (10) are filled respectively with the first and second components (24, 26) of the composition. Then, a twist cap (90) is placed over the distal end of the syringe (10) to seal the syringe (10) during shipping and storage. When the dentist or other clinician is ready to use the syringe (10), he or she twists the cap (90) off the syringe (10), places the dispensing tip (18) thereon, and dispenses the material accordingly. Then, the user removes the dispensing tip (18) and places the cap back over the end of the syringe (10) so that the syringe (10) may be stored. The twist cap (90) can be applied or removed by firmly grasping finger handle (92) and exerting a turning motion. Alternatively, the user can leave the dispensing tip (18) on the syringe "as is", until he or she is ready to use the syringe (10) again. Then, the user will replace the old dispensing tip (18) on the syringe (10) with a new dispensing tip (18). Conventional dispensing tips, known in the industry, may be used with the dispensing syringe (10) of this invention. Such dispensing tips (18) typically include a static mixing element for combining and mixing the first and second components (24, 26) together. The composition containing the combined first and second components (24, 26) then is dispensed through the nozzle (19) and onto the given area. The dispensing tip (18) is secured over the exit ports (32, 38) of the first and second barrels (20, 22) so that the tip (18) can receive the first and second components (24, 26) and dispense them accordingly. Dispensing tips (18) containing static mixing elements are valuable, because they can mix the components (24, 26) before dispensing the composition. The syringe (10) can be used without any dispensing tip (18). In such instances, where the syringe (10) does not contain a dispensing tip (18), the components (24, 26) are dispensed from the first and second barrels (20, 22) onto a mixing pad or the like. Then, the components (24, 26) can be mixed together using a spatula or other conventional mixing device to form a mixed composition ready for use.

In practice, a dental professional can hold the syringe body (12) in one hand. He or she can then pinch the connector knob (16) between his/her thumb and finger of the other hand and rotate the knob (16) accordingly. In the syringe device (10) shown in FIG. 8, if the knob (16) is rotated in a clockwise direction, the first and second plunger rods (30, 36) will advance in a forward direction to force the first and second components (24, 26) into the dispensing tip (18). The first and second components (24, 26) can be any dental composition. For example, the first component (24) can be a base material and the second component (26) can be a catalyst material. The base material (24) can be stored in the first barrel (20), and the catalyst material (26) can be stored in the second barrel (22). When the dental professional wishes to form the mixed dental composition, he or she rotates the connector knob (16) to force the base and catalysts materials into the dispensing tip (18). The base and catalyst materials are mixed by the mixing element in the dispensing tip (18) to produce the desired mixed composition. The dental professional then dispenses the resultant composition through the dispensing tip (18) and to the targeted area.

One benefit of the syringe (10) of this invention is that the dental professional can accurately control the dosage being dispensed. The connector knob (16) provides good tactile feedback to the practitioner as he/she turns the knob (16) to dispense the composition. This tactile feedback helps the user to more accurately sense and control the amount of composition being delivered. Also, it is possible to dispense the composition in a precisely metered quantity by rotating the connector knob (16) to a desired point along the plunger rod assembly (14). For example, if desired, the knob (16) can be rotated to the point where the rigid plate (44) contacts the connector knob (16). Because of the mechanical advantage gained by using the screw threads of the connector knob (16) and plunger rods (30, 36), a dental professional can dispense relative thick dental compositions with the syringe (10) of this invention. Furthermore, the screw threads provide ergonomic benefits, because the practitioner does not need to apply excessive force to the plunger rods (30, 36). Rather, the practitioner can simply and easily rotate the connector knob (16) to actuate the plunger rods (30, 36) and discharge the composition.

It is understood that the syringe devices described and illustrated herein represent only presently preferred embodiments of the invention. It is appreciated by those skilled in the art that various changes and additions can be made to such syringe devices without departing from the spirit and scope of this invention. For example, the syringe device could be constructed so that it included more than two barrels for dispensing the dental composition. More particularly, a three (3) or four (4) barrel syringe could be constructed for dispensing a three or four component dental composition. Furthermore, although the syringe devices of this invention have been described herein primarily as being suitable for dispensing a multi-component dental composition, particularly a composition comprising a base paste and catalyst paste, it should be understood that the syringes can be used to dispense other multi-component compositions. For example, the syringe devices can be used to dispense multi-component compositions of epoxy cements, adhesives, and medicaments. Using the syringe device to dispense a multi-component dental composition represents only one of the many possible ways that the syringes of this invention can be used. It is intended that all such embodiments be covered by the appended claims.

What is claimed is:

1. A dispensing syringe for dispensing a two-component composition, comprising:
    a) a syringe body including,
        i) a first elongated barrel having a proximate opening for receiving a first plunger rod and a first exit port for discharging a first component of the composition;
        ii) a second elongated barrel having a proximate opening for receiving a second plunger rod and a second exit port for discharging a second component of the composition, the first and second barrels being arranged in parallel along the length of the syringe body;
    b) a plunger rod assembly including,
        i) a rearward stop plate,
        ii) a first plunger rod having an outer threaded edge and an inner non-threaded edge, the first plunger rod having a forward-facing end portion for forcing the first component of the composition into the first exit port, and an opposing rear-facing end portion attached to the stop plate,
        iii) a second plunger rod having an outer threaded edge and an inner non-threaded edge, the second plunger rod having a forward-facing end portion for forcing the second component of the composition into the second exit port, and an opposing rear-facing end portion attached to the stop plate, wherein the first and second plunger rods are arranged in parallel for joint movement within the first and second barrels respectively; and
    c) a rotatable, threaded knob for connecting the plunger rod assembly to the syringe body, the threaded knob having a through-bore with a continuous internal thread for engaging the outer threaded edges of the first and second plunger rods so that only the knob is rotated and the syringe body remains stationary and as the knob is rotated about the longitudinal axis of the syringe body, the plunger rods move together in a forward or rearward direction within the barrels,
    wherein the syringe body further comprises a central supporting member having a pair of inner grooved segments for receiving radial fins extending along the inner surfaces of the first and second plunger rods and guiding the plunger rods into the first and second barrels respectively.

2. The dispensing syringe of claim 1, wherein the syringe is used to dispense a two component dental composition.

3. The dispensing syringe of claim 2, wherein one component of the dental composition is a base paste and the second component is a catalyst paste.

4. The dispensing syringe of claim 2, wherein the dental composition is a dental cement.

5. The dispensing syringe of claim 1, wherein the first and second barrels have cylindrical structures.

6. The dispensing syringe of claim 1, wherein the first and second exit ports are cylindrically-shaped.

7. The dispensing syringe of claim 1, wherein the first and second exit ports are semi-circular shaped.

8. The dispensing syringe of claim 1, wherein the inner edges of the first and second plunger rods each includes a radial fin, each radial fin extending along a length of the respective edge and radiating at an angle of about ninety degrees to the edge.

9. The dispensing syringe of claim 1, wherein the first and second plunger rods each includes a piston attached to their forward-facing end portions for forcing the first and second components of the composition into the first and second exit ports respectively.

10. The dispensing syringe of claim 1, wherein the syringe body further comprises a ledge having a recessed area for receiving the rotatable threaded knob that connects the plunger rod assembly to the syringe body.

11. The dispensing syringe of claim 10, wherein the ledge is circular-shaped and surrounds the first and second barrels of the syringe body.

12. The dispensing syringe of claim 10, wherein the rotatable knob includes a locking flange so that the knob can be snap-fitted into the recessed area of the ledge on the syringe body.

13. A dispensing syringe for dispensing a two-component composition, comprising:
   a) a syringe body including,
      i) a first elongated barrel having a proximate opening for receiving a first plunger rod and a first exit port for discharging a first component of the composition into a dispensing tip;
      ii) a second elongated barrel having a proximate opening for receiving a second plunger rod and a second exit port for discharging a second component of the composition into the dispensing tip, the first and second barrels being arranged in parallel along the length of the syringe body;
   b) a plunger rod assembly including,
      i) a rearward stop plate,
      ii) a first plunger rod having an outer threaded edge and an inner non-threaded edge, the first plunger rod having a forward-facing end portion for forcing the first component of the composition into the dispensing tip, and an opposing rear-facing end portion attached to the stop plate,
      iii) a second plunger rod having an outer threaded edge and an inner non-threaded edge, the second plunger rod having a forward-facing end portion for forcing the second component of the composition into the dispensing tip, and an opposing rear-facing end portion attached to the stop plate, wherein the first and second plunger rods are arranged in parallel for joint movement within the first and second barrels respectively;
   c) a rotatable, threaded knob for connecting the plunger rod assembly to the syringe body, the threaded knob having a through-bore with a continuous internal thread for engaging the outer threaded edges of the first and second plunger rods so that only the knob is rotated and the syringe body remains stationary and as the knob is rotated about the longitudinal axis of the syringe body, the plunger rods move together in a forward or rearward direction within the barrels, and
   d) a dispensing tip for receiving the first and second components of the composition from the first and second barrels and dispensing the composition to a desired area,
   wherein the syringe body further comprises a central supporting member having a pair of inner grooved segments for receiving radial fins extending along the inner surfaces of the first and second plunger rods and guiding the plunger rods into the first and second barrels respectively.

14. The dispensing syringe of claim 13, wherein the dispensing tip includes a static mixer element.

15. The dispensing syringe of claim 13, wherein the syringe is used to dispense a two component dental composition.

16. The dispensing syringe of claim 15, wherein one component of the dental composition is a base paste and the second component is a catalyst paste.

17. The dispensing syringe of claim 15, wherein the dental composition is a dental cement.

18. A dispensing syringe for dispensing a multi-component composition, comprising:
   a) a syringe body including multiple elongated barrels, each barrel having a proximate opening for receiving a plunger rod and an exit port for discharging a single component of the composition;
   b) a plunger rod assembly including,
      i) a rearward stop plate,
      ii) multiple plunger rods, each plunger rod having an outer threaded edge and an inner non-threaded edge, and each plunger rod further having a forward-facing end portion for forcing a single component of the composition into an exit port, and an opposing rear-facing end portion attached to the stop plate, wherein the plunger rods are arranged for joint movement within the barrels; and
   c) a rotatable, threaded knob for connecting the plunger rod assembly to the syringe body, the threaded knob having a through-bore with a continuous internal thread for engaging the outer threaded edges of the multiple plunger rods so that only the knob is rotated and the syringe body remains stationary and as the knob is rotated about the longitudinal axis of the syringe body, the plunger rods move together in a forward or rearward direction within the barrels,
   wherein the syringe body further comprises a central supporting member having a pair of inner grooved segments for receiving radial fins extending along the inner surfaces of the first and second plunger rods and guiding the plunger rods into the first and second barrels respectively.

19. The dispensing syringe of claim 18, wherein the syringe includes a dispensing tip.

20. The dispensing syringe of claim 19, wherein the dispensing tip includes a static mixer element.

21. The dispensing syringe of claim 18, wherein the syringe is used to dispense a multi-component dental composition.

* * * * *